United States Patent
Bonne et al.

(10) Patent No.: US 7,975,525 B2
(45) Date of Patent: Jul. 12, 2011

(54) SELF-CALIBRATING SENSOR

(75) Inventors: Ulrich Bonne, Hopkins, MN (US);
Peter Tobias, Minnetonka, MN (US);
Aravind Padmanabhan, Plymouth, MN (US); Thomas M. Rezachek, Cottage Grove, MN (US)

(73) Assignee: Honeywell International Inc., Morristown, NJ (US)

( * ) Notice: Subject to any disclaimer, the term of this patent is extended or adjusted under 35 U.S.C. 154(b) by 352 days.

(21) Appl. No.: 11/803,968

(22) Filed: May 16, 2007

(65) Prior Publication Data

US 2008/0282765 A1  Nov. 20, 2008

(51) Int. Cl.
*G01N 21/00* (2006.01)
(52) U.S. Cl. ........................................ 73/1.07
(58) Field of Classification Search ................... 73/1.07, 73/1.06
See application file for complete search history.

(56) References Cited

U.S. PATENT DOCUMENTS

| | | | |
|---|---|---|---|
| 3,557,532 A | | 1/1971 | Arthur |
| 4,063,446 A | | 12/1977 | Fuhrmann et al. |
| 4,314,344 A | * | 2/1982 | Johns et al. ............... 73/1.03 |
| 4,829,809 A | | 5/1989 | Tantram et al. |
| 5,395,501 A | | 3/1995 | Rohrbacker et al. |
| 5,469,369 A | * | 11/1995 | Rose-Pehrsson et al. ..... 73/23.2 |
| 5,741,413 A | | 4/1998 | Capetanopoulos |
| 5,761,952 A | | 6/1998 | Gilby et al. |
| 6,393,894 B1 | | 5/2002 | Bonne et al. |
| 6,553,808 B2 | | 4/2003 | Bonne et al. |
| 6,715,339 B2 | | 4/2004 | Bonne et al. |
| 7,000,452 B2 | | 2/2006 | Bonne et al. |
| 7,073,368 B2 | | 7/2006 | Wood et al. |
| 7,104,112 B2 | | 9/2006 | Bonne et al. |
| 2004/0194628 A1 | | 10/2004 | Mitra |
| 2005/0217672 A1 | * | 10/2005 | Bengtsson et al. ....... 128/204.18 |
| 2006/0263254 A1 | | 11/2006 | Lee |

FOREIGN PATENT DOCUMENTS

| | | |
|---|---|---|
| DE | 0159616 A1 | 6/2003 |
| DE | 10159616 A1 | 6/2003 |
| FR | 2708995 | 2/1995 |
| FR | 2708995 A1 | 2/1995 |
| WO | WO-01/040793 A1 | 6/2001 |
| WO | WO-0140793 | 6/2001 |
| WO | WO-00140793 A1 | 6/2001 |

OTHER PUBLICATIONS

"European Application Serial No. 08156196.1, European Search Report mailed Jan. 22, 2009", 3 pgs.
"European Application Serial No. 08156196.1, Communication mailed Apr. 1, 2009", 3 pgs.
"European application Serial No. 08156196 Office Action Mailed Dec. 4, 2009", 3 pgs.
Ohira, S., et al., "In situ gas generation for micro gas analysis system", Analytica Chimica Acta, 588(1), (Apr. 4, 2007), 147-152.

* cited by examiner

*Primary Examiner* — Hezron Williams
*Assistant Examiner* — Alex Devito
(74) *Attorney, Agent, or Firm* — Schwegman, Lundberg & Woessner P.A.

(57) ABSTRACT

Embodiments of the present invention relate to a gas sensor comprising a flow channel, a concentration modulator positioned in the flow channel, a gas generator in contact with the flow channel, one or more gas detectors positioned downstream of the concentration modulator and gas generator and a pump.

27 Claims, 4 Drawing Sheets

SELF-CALIBRATING SENSOR

TECHNICAL FIELD

Embodiments of the present invention relate to a self-calibrating sensor. More specifically, embodiments of the present invention relate to a self-calibrating gas sensor for trace analyte detection.

BACKGROUND

The reliability of toxic gas detectors is of great importance in many applications, especially when these instruments are used for ensuring the safety of personnel. Reliability is typically obtained by periodic checking of the instrument response to a test gas, however calibration test gases are typically supplied in large, bulky and expensive gas cylinders.

Potentially hazardous atmospheres are found in many locations, due to the presence of toxic gases, combustible gas mixtures or the excess or deficiency of oxygen concentration. Many types of gas detection instruments have been developed to provide a warning that the atmosphere contains potentially hazardous components, or to initiate remedial action. Examples of these gas detection instruments include the detection of combustible gases in coal mines, hydrogen sulfide in oil fields and water treatment plants, carbon monoxide in places ranging from steel mills to bedrooms, and oxygen in confined spaces, such as sewers. Within each gas detection instrument there are one or more gas sensors, whose function is to provide an electrical signal, which varies in response to the gas concentration.

Most gas sensors provide a relative output signal, such that the output signal is not an absolute measure of gas concentration, but merely proportional to the gas concentration. In such cases, the gas sensor must be calibrated with a known test gas prior to use. Calibration can also be used as a function check to ensure the sensor is working. The output from many types of sensors can vary over time and sensors can fail to operate without warning. Such sensors may suffer from unpredictable baseline drift and span drift. If the sensor is not sensitive or fast enough, unacceptable undetected toxic analyte events or high False Alarm Rates (FAR) may occur. Frequently, calibrating a gas sensor can be time consuming, expensive and cumbersome in many applications.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

SUMMARY

Figure 1:
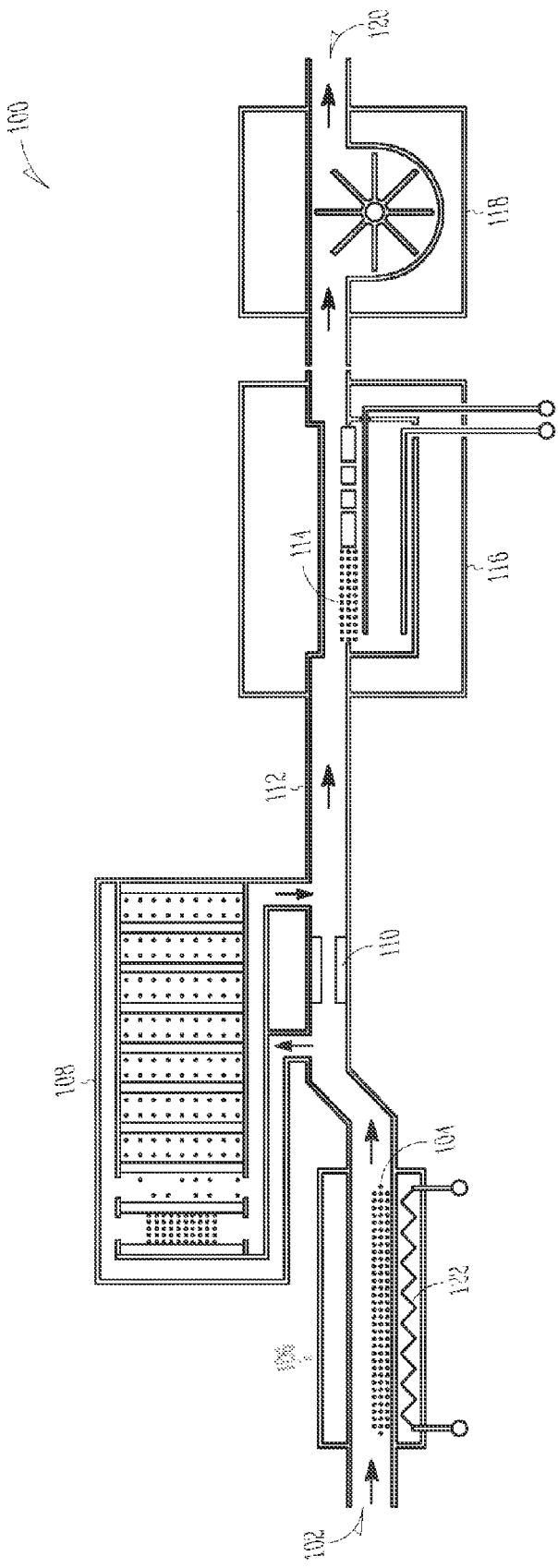
FIG. 1 illustrates a schematic of a self-calibrating sensor, according to some embodiments.

Embodiments of the present invention relate to a gas sensor comprising a flow channel, a concentration modulator positioned in the flow channel, a gas generator in contact with the flow channel, one or more gas detectors positioned downstream of the concentration modulator and gas generator and a pump.

Embodiments also relate to a method of detecting a gas. The method comprises introducing a sample gas, adsorbing a least a portion of the sample sufficient to provide an adsorbed sample and a flow-through sample, detecting the flow-through sample sufficient to provide a flow-through electrical signal, releasing the adsorbed sample, detecting the adsorbed sample sufficient to provide an adsorbed sample electrical signal, generating a calibration sample and detecting a calibration sample sufficient to provide a calibration sample electrical signal.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Embodiments of the invention relate to a self-calibrating gas sensor and methods of detecting a gas. The self-calibrating sensor includes continuous baseline drift removal, continuous resetting of its intrinsic baseline readout, fully automated span self-calibration and pre-concentration to increase sensor sensitivity. The sensor incorporates a concentration modulator that acts as a pre-concentrator and analyte modulator, for increased sensitivity and baseline drift removal. During a periodic adsorption period, the sensor can self-generate a calibration gas for resetting of the baseline. In addition, the sensor includes fully automated span self-calibration. Because such features are integrated in a single sensor system that can be reduced to micro size, reliability and sensitivity are achieved in a sensor with low cost and little maintenance.

Referring to FIG. 1, a schematic of a self-calibrating sensor 100 is shown, according to some embodiments. A flow channel 112, including an inlet 102 and outlet 120, may be in contact with a concentration modulator 106. The modulator may include a heater 122 and an adsorber 104, for example. The flow channel 112 may also be in contact with a gas generator 108. The gas generator 108 may be used in conjunction with a flow restrictor 110. A detector 116 and pump 118 may be positioned in contact with the flow channel 112. The detector 116 may utilize a permeable membrane 114.

A concentration modulator 106 may act as a pre-concentrator and an analyte modulator. The concentration modulator 106 may include an adsorber 104 in contact with a heater 122. Examples of adsorbers 104 include a film, resin, capillary or column, for example. Adsorbers may be characterized by their breakthrough volume (BTV), the volume of a carrier gas per unit weight of adsorbent which causes the analyte to migrate from the front to back of an adsorbent bed. The heater 122 may be a thin film or wire, for example. The type of adsorber may be selective to the target analyte or analytes.

The detector 116 may be an electrochemical detector, for example. The detector 116 may be a combustible gas detector, such as a pellistor. The detector 116 may also be a semiconducting oxide.

Figure 2:
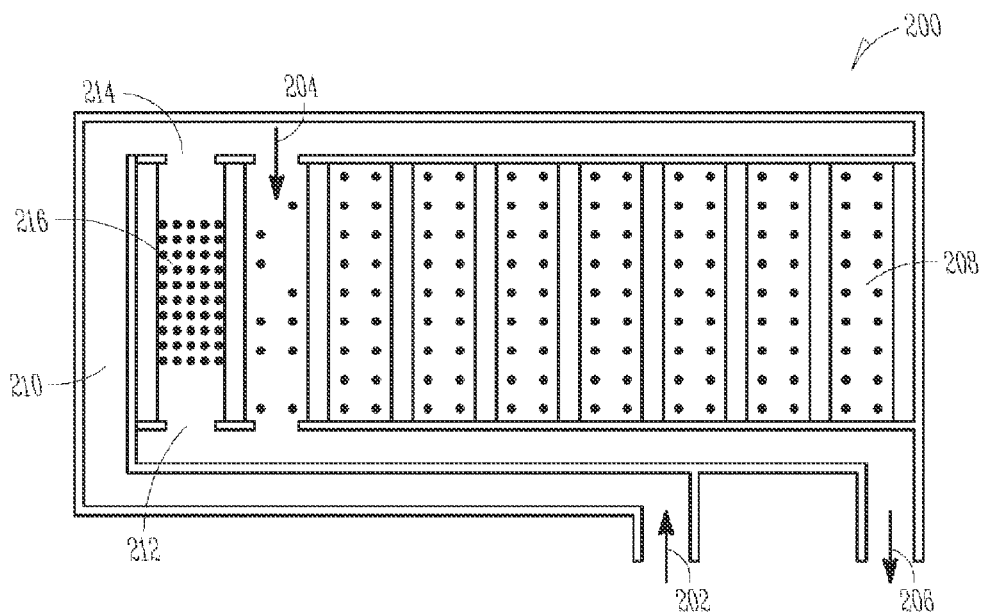
FIG. 2 illustrates a schematic of a gas generator, according to some embodiments.

An example of a gas generator 108 is shown in FIG. 2. The sample gas may enter generator through inlet 202. A restrictor 210, such as a plug or valve, may be positioned in the channel to control movement of the sample. Membranes 212, 214 may be controlled by heat or electronics to rupture and initiate a gas generation reaction. Each reactor 208 may contain reagents 216 that when activated or chemically reacted, release a calibration gas. The sample may flow 204 through the calibration gas and back to the flow channel through outlet 206. The reactors 208 may form an array, for example. The calibration gas generated may be methane, pentane, propane, carbon monoxide or carbon dioxide, for example. A restrictor or plug 210 may be utilized if the volume or flush time of the generated gas are relatively large compared to the dead end volume of the detector and desorption peaks, for example.

Examples of reactions to generate a calibration gas include:

$NaOH+NaCOOCH_3 \Rightarrow Na_2CO_3+CH_4$

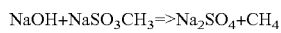
$NaOH+NaSO_3CH_3 \Rightarrow Na_2SO_4+CH_4$

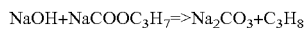
$NaOH+NaCOOC_3H_7 \Rightarrow Na_2CO_3+C_3H_8$

$NaOH+NaCOOC_5H_{11} \Rightarrow Na_2CO_3+C_5H_{12}$

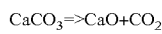
$CaCO_3 \Rightarrow CaO+CO_2$

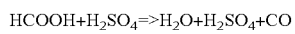
$HCOOH+H_2SO_4 \Rightarrow H_2O+H_2SO_4+CO$

Examples of gas generating devices and methods of generating a calibration gas may be found in commonly owned U.S. patent application Ser. No. 11/618,398, entitled "GAS GENERATION FOR SENSOR CALIBRATION"; U.S. patent application Ser. No. 11/618,404, entitled "GAS SENSOR TEST SYSTEM AND METHODS RELATED THERETO"; and U.S. patent application Ser. No. 11/618,414, entitled "GAS SENSOR CALIBRATION FROM FLUID", all filed Dec. 29, 2006 and incorporated herein in their entirety.

Figure 3:
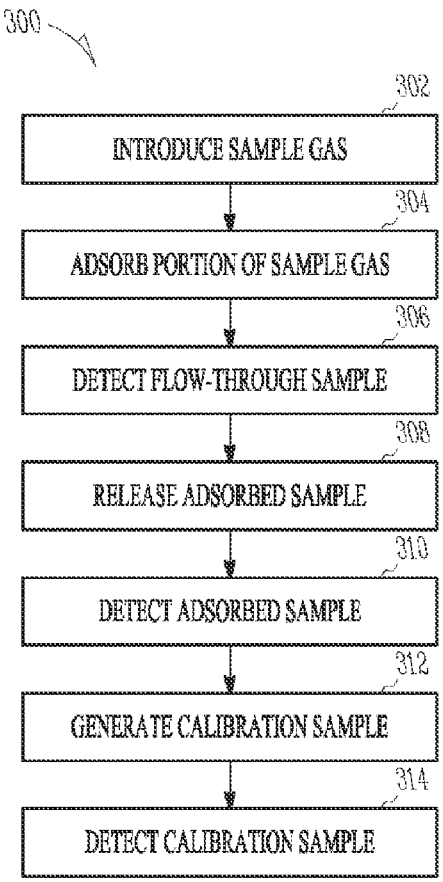
FIG. 3 illustrates a block flow diagram of a method of detecting a gas, according to some embodiments.

Referring to FIG. 3, a block flow diagram of a method 700 of detecting a gas is shown, according to some embodiments. A sample gas may be introduced 302 to a flow channel. At least a portion of the sample gas may be adsorbed 304, sufficient to provide an adsorbed sample and a flow-through sample. The flow-through sample may be detected 306, sufficient to provide a flow-through sample electrical signal. The adsorbed sample may be released 308 and detected 310, sufficient to provide an adsorbed sample electrical signal. A calibration sample 312 may be generated 312 and detected 314, sufficient to provide a calibration sample electrical signal.

A sample gas may be introduced 302 by injecting or pumping, for example. The sample gas may be introduced 302 to a flow channel by ambient contact. The sample gas may be continuously introduced, such as being drawn continuously by a pump.

The sample gas may be adsorbed 304 by contacting an adsorber, such as a film positioned in the channel. The target analytes may be physically or chemically bound to the adsorber, for example. Adsorbing 304 a portion of the sample concentrates the target analytes in a predictable and detectable way, thus increasing the sensitivity of the sensor system. The adsorber may also be used as an analyte modulator, assisting in the substantial reduction of baseline drift. Examples of analyte modulation and sensors incorporating such features may be found in commonly owned U.S. Patent Application Ser. No. 60/866,182, entitled "SENSOR WITH ANALYTE MODULATOR", filed Nov. 16, 2006, the disclosure of which is herein incorporated in its entirety.

The flow-through sample may be detected 306. As the portion of the sample that is not adsorbed by the adsorber, the flow-through sample may continue to the detector where detection 306 occurs. The detector may convert a detection signal, such as a chemical signal, to an electronic signal. An electronic filter may be used to filter the flow-through sample signal, thus decreasing or substantially eliminating baseline drift. By adsorbing a portion of the sample, an adsorbed sample and flow-through sample have differing detection signals and corresponding electrical signals, such as AC output. The slower flow-through sample signal may be electronically filtered out from the adsorbed sample signal, for example.

The adsorbed sample may be released 308. In contact with the adsorber, may be a heater. The heater may be controlled to cycle on and off. The heater may be on about 50% of the time a sample is introduced 302, for example. The heater may be on about 10% of the time, about 20% of the time, about 30% of the time or about 40% of the time a sample is introduced 302, for example. Heating the adsorber may release 308 an adsorbed sample. Allowing the adsorber to reach a saturation point and continuing to contact the adsorber may create a breakthrough of sample through the flow channel. The portion of the sample that is not adsorbed may be termed the flow-through sample, which continues through the channel.

Once the adsorbed is released 308, it may travel to the detector to be detected 310 or it may be routed to a gas generator before detection 310. The use of a flow restrictor in the flow channel may assist in directing the adsorbed sample to the gas generator. The gas generator may generate 312 a calibration sample that contacts the adsorbed sample. The combined sample may be detected 314. The calibration sample may be generated 312 before or after the flow of the adsorbed sample and detected 314. By utilizing a known amount of calibration sample, span drift may be substantially decreased. An example of such span correction may occur when the heating element or releasing mechanism is in an "off" cycle. By cycling the heating or releasing, the modulation of the analyte in combination with the generation of a calibration gas, provides a target signal that is substantially removed of baseline drift and span drift and the sensor has an increased sensitivity. The steps are repeatable for as long as a sample gas is introduced or continuously fed to the sensor.

EXAMPLES

Figure 4:
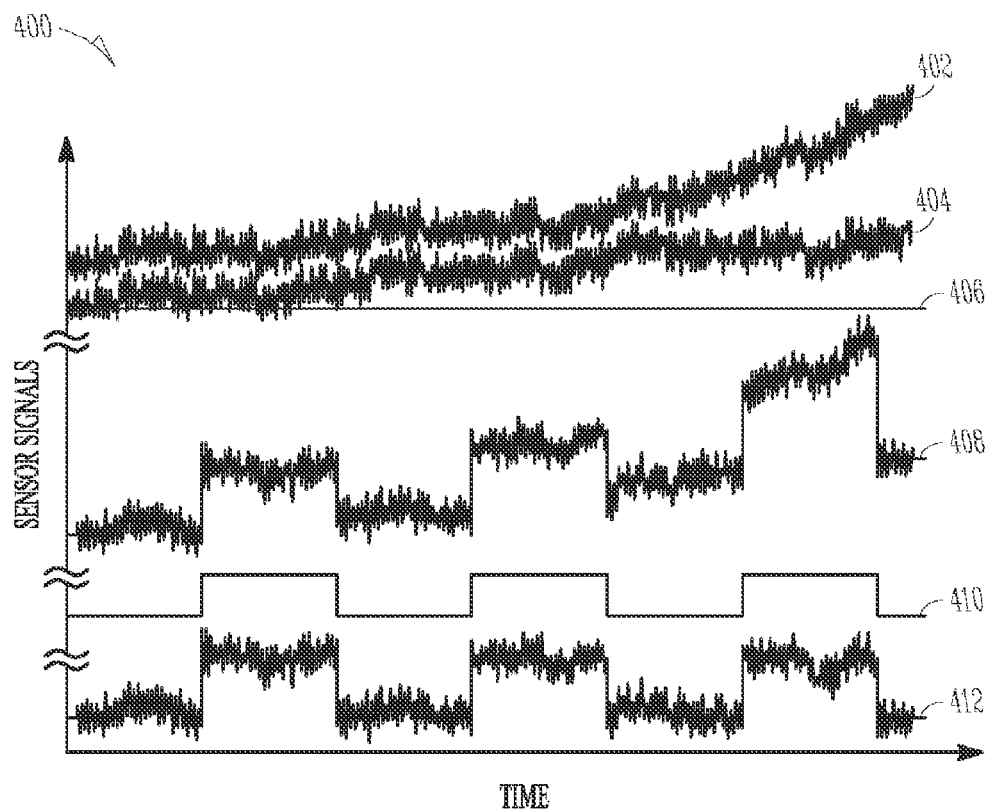
FIG. 4 illustrates a graphical representation of self-calibrating sensor signals, according to some embodiments.

Referring to FIG. 4, a graphical representation 400 of self-calibrating sensor signals is shown, according to some embodiments. Signal 402 represents a signal with baseline and span drifts. Signal 404 shows a signal with span drift. A theoretical baseline with no drift is shown by signal 406. Analyte modulation without removing drift is shown in signal 408. Signal 410 shows the cycling of a heater or releasing mechanism. The signal 412 displays a corrected modulated signal after removing baseline and span drifts.

Figure 5:
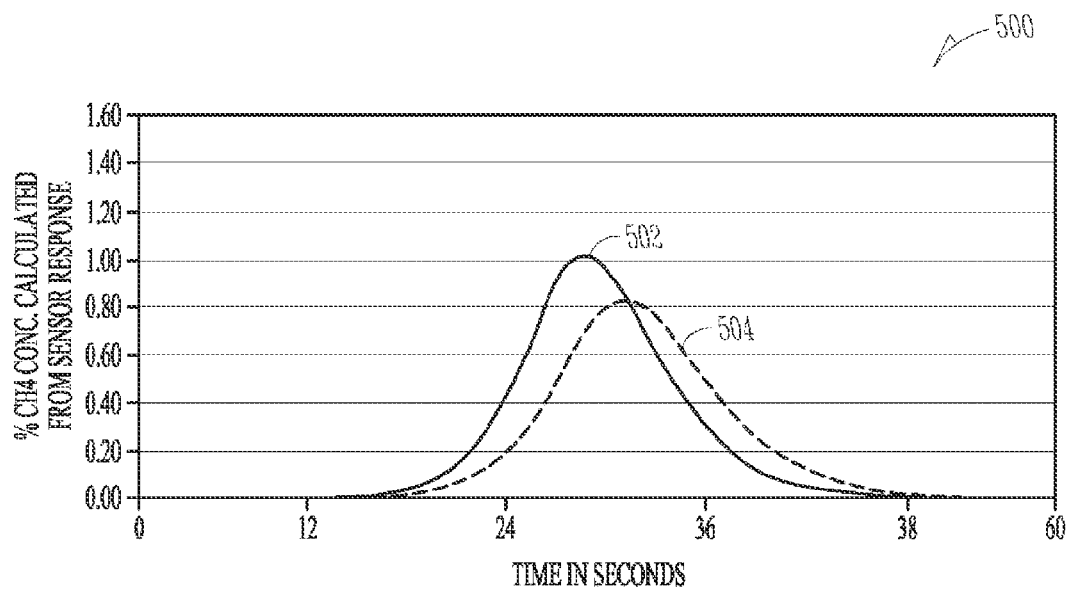
FIG. 5 illustrates a graphical representation of gas generation, according to some embodiments.

Referring to FIG. 5, a graphical representation 500 of gas generation is shown, according to some embodiments. Signals 502 and 504 are signals from two catalytic bead sensors, sensing the methane gas generated from an acetate reaction. Signal 504 is from a sensor downstream from sensor of signal 502. The generated gas reaches the sensor of signal 504 later, and the gas concentration is smaller, because a portion of the gas has been consumed at the sensor of signal 502. The sensor of signal 504 may have lost sensitivity during the measurement series, so a new calibration may be desirable.

Figure 6:
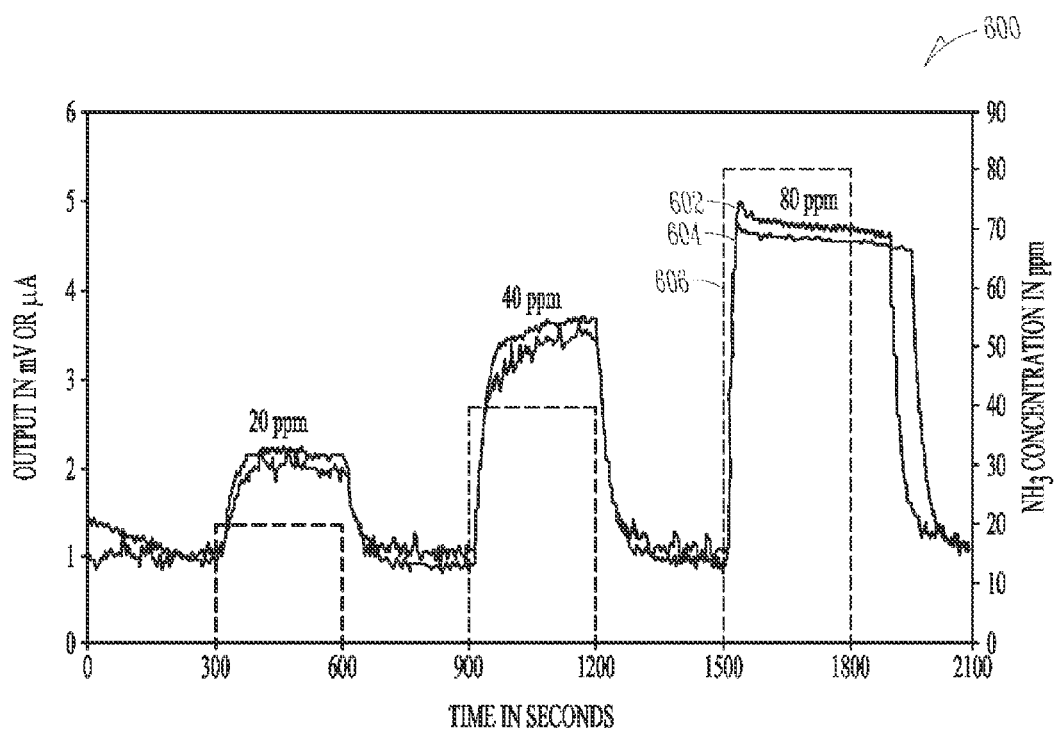
FIG. 6 illustrates a graphical representation of a sensor response, according to some embodiments.

Referring to FIG. 6, a graphical representation 600 of a sensor response is shown, according to some embodiments. Signals 602 and 604 represent two sensors detecting a calibrated ammonia signal in synthetic air at 50% relative humidity. Signal 606 represents the know calibration gas concentration, as produced by the gas generator.

Figure 7:
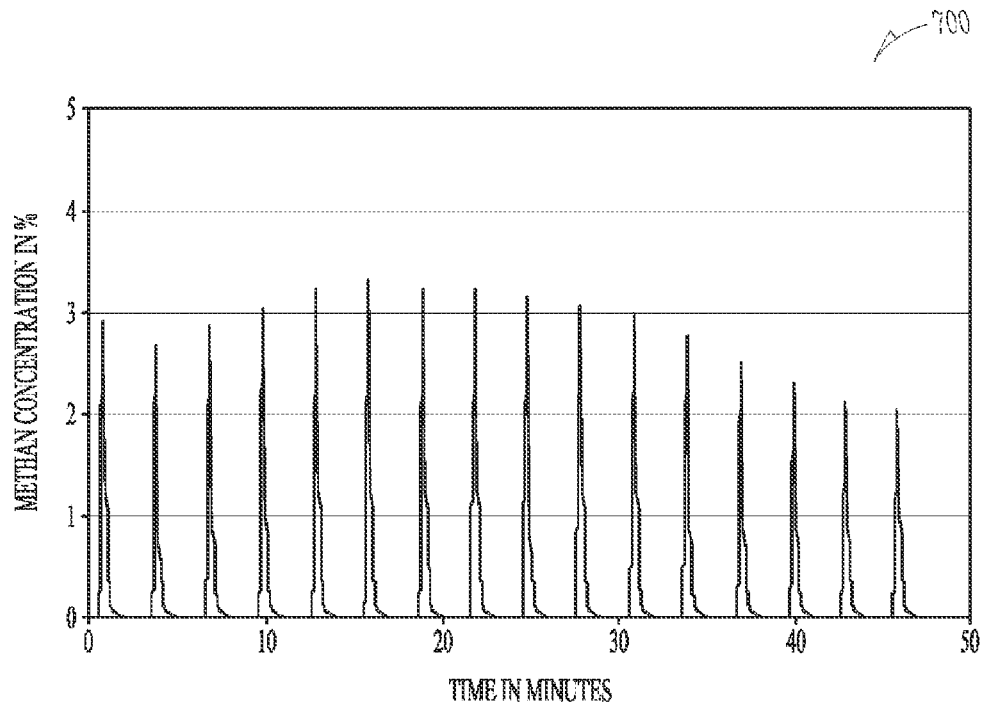
FIG. 7 illustrates a graphical representation of gas pulses, according to some embodiments.

Referring to FIG. 7, a graphical representation 700 of gas pulses is shown, according to some embodiments. Methane gas pulses were generated by repeated heating of a 0.1 cm$^3$ reactant volume and detected by a catalytic bead sensor.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

What is claimed is:

1. A self-calibrating gas sensor, comprising:
   a flow channel;
   a concentration modulator, positioned in the flow channel;
   a gas generator adapted to self-generate a calibration gas for resetting a baseline without a known test gas, wherein the gas generator is integrated with and in contact with the flow channel having an inlet coupled to the flow channel to receive a sample gas, and an outlet to provide the received sample gas and calibration gas back into the flow channel downstream from the inlet in the flow channel;
   one or more gas detectors, positioned downstream of the concentration modulator and gas generator; and
   a pump.

2. The gas sensor of claim 1, wherein the concentration modulator comprises a heater and an adsorber.

3. The gas sensor of claim 2, wherein the adsorber comprises a film.

4. The gas sensor of claim 2, wherein the adsorber comprises a capillary.

5. The gas sensor of claim 2, wherein the adsorber comprises a column.

6. The gas sensor of claim 1, wherein the gas generator comprises a methane gas generator.

7. The gas sensor of claim 1, wherein the gas generator comprises a propane gas generator.

8. The gas sensor of claim 1, wherein the gas generator comprises a pentane gas generator.

9. The gas sensor of claim 1, wherein the gas generator comprises a carbon monoxide gas generator.

10. The gas sensor of claim 1, wherein the gas generator comprises a carbon dioxide gas generator.

11. The gas sensor of claim 1, wherein the one or more detectors comprise electrochemical detectors.

12. A gas self-calibrating sensor, comprising:
    a flow channel;
    a concentration modulator, positioned in the flow channel, the concentration modulator receiving a sample gas and providing the sample gas and an adsorbed gas into the flow channel;
    a gas generator adapted to generate a calibration gas in response to an adsorbed gas received from the concentration modulator, the gas generator having an input and an output spaced apart along and coupled to the flow channel to receive the sample gas flowing through the flow channel and to self-generate a calibration gas and add the calibration gas to the sample gas flowing through the flow channel at the output positioned downstream from the input;
    one or more gas detectors, positioned downstream of the concentration modulator and gas generator; and
    a pump.

13. The gas sensor of claim 12 and further comprising a flow restrictor within the flow channel between the input and output of the gas generator.

14. The gas sensor of claim 12, wherein the concentration modulator comprises a heater and an adsorber, and wherein the concentration modulator cycles the heater on and off.

15. The gas sensor of claim 14, wherein the adsorber comprises a film.

16. The gas sensor of claim 12, wherein the gas generator comprises a methane gas generator.

17. The gas sensor of claim 1 and further comprising a restrictor positioned in the flow channel between the flow channel coupled gas generator inlet and outlet to periodically release an output of the concentration modulator to the one or more gas detectors.

18. The gas sensor of claim 12 and further comprising a restrictor positioned in the flow channel between the flow channel coupled gas generator inlet and outlet, the restrictor directing the adsorbed gas to the gas generator.

19. The gas sensor of claim 18 wherein heat cycling of the concentration modulator releases the adsorbed gas.

20. The gas sensor of claim 19 wherein heat cycling of the concentration modulator modulates removes baseline drift of an output gas.

21. A self-calibrating sensor, comprising:
    a modulator, comprising:
      an adsorbing mechanism to adsorb at least a least a portion of a sample gas to provide an adsorbed sample and a flow-through sample;
      a releasing mechanism to periodically release the adsorbed sample from the modulator;
    a gas generator coupled to the concentration modulator and adapted to self-generate a calibration sample from the adsorbed sample received from the modulator;
    a detector coupled to the gas generator and the modulator to receive the flow-through sample from the modulator and the calibration sample from the gas generator; and
    a restrictor coupled between the modulator and the detector and adapted to restrict the flow-through sample when the detector is detecting the calibration sample.

22. The self-calibrating sensor of claim 21, wherein detection of the calibration sample corrects for baseline drift.

23. The self-calibrating sensor as in claim 21, wherein the releasing mechanism is a heater which cycles on and off.

24. The self-calibrating sensor as in claim 21, wherein the gas generator includes a flow restrictor and an adsorbing mechanism.

25. The self-calibrating sensor as in claim 21, wherein the detector is adapted to generate an electronic signal.

26. The self-calibrating sensor as in claim 21 and further comprising an electronic filter to filter an electronic signal associated with the flow-through sample to remove baseline drift.

27. The self-calibrating sensor as in claim 21, wherein the flow-through sample is that portion of the sample gas that is not adsorbed.

* * * * *